United States Patent
McDermott et al.

(10) Patent No.: US 11,207,117 B2
(45) Date of Patent: Dec. 28, 2021

(54) SYSTEMS AND METHODS TO ENSURE GAS EGRESS DURING CRYOTHERAPY

(71) Applicant: CSA Medical, Inc., Lexington, MA (US)

(72) Inventors: Sean A. McDermott, Weymouth, MA (US); Charles J. Vadala, Boston, MA (US); Brian M. Hanley, Reading, MA (US); John P. O'Connor, Andover, MA (US)

(73) Assignee: CSA Medical, Inc., Lexington, MA (US)

( * ) Notice: Subject to any disclaimer, the term of this patent is extended or adjusted under 35 U.S.C. 154(b) by 593 days.

(21) Appl. No.: 15/914,507

(22) Filed: Mar. 7, 2018

(65) Prior Publication Data
US 2018/0256236 A1 Sep. 13, 2018

Related U.S. Application Data

(60) Provisional application No. 62/468,631, filed on Mar. 8, 2017.

(51) Int. Cl.
*A61B 18/02* (2006.01)
*A61M 16/04* (2006.01)
(Continued)

(52) U.S. Cl.
CPC ...... *A61B 18/0218* (2013.01); *A61B 17/3415* (2013.01); *A61B 17/3474* (2013.01);
(Continued)

(58) Field of Classification Search
CPC ............ A61B 17/3415; A61B 17/3474; A61B 18/0218; A61B 2017/345; A61B 2018/00166; A61B 2018/00172; A61B 2018/00273; A61B 2018/00541; A61B 2018/00577; A61B 2018/00642; A61B 2018/00708; A61B 2018/00863;
(Continued)

(56) References Cited

U.S. PATENT DOCUMENTS

| | | | |
|---|---|---|---|
| 8,777,936 B2 * | 7/2014 | Fischer | A61B 18/02 606/21 |
| 2002/0143323 A1 * | 10/2002 | Johnston | A61B 34/35 606/21 |

(Continued)

FOREIGN PATENT DOCUMENTS

| | | |
|---|---|---|
| JP | 2007136031 A | 6/2007 |
| JP | 2016508820 A | 3/2016 |

OTHER PUBLICATIONS

International Search Report and Written Opinion for PCT/US2018/021325 dated Aug. 31, 2018 (22 pages).

*Primary Examiner* — Michael F Peffley
(74) *Attorney, Agent, or Firm* — Kacvinsky Daisak Bluni PLLC (57) ABSTRACT

The present disclosure relates generally to the field of cryotherapy. In particular, the present disclosure relates to cryotherapy systems that ensure egress of cryogen gas delivered within a patient's body during cryotherapy procedures and, more particularly, sensors for use with cryotherapy systems that include delivery catheters wherein the systems ensure that egress of cryogen gas from the patient's body is possible whenever the catheter is operating.

19 Claims, 10 Drawing Sheets

(51) Int. Cl.
*A61M 16/20* (2006.01)
*A61M 16/08* (2006.01)
*A61B 17/34* (2006.01)
A61B 18/00 (2006.01)
A61B 90/00 (2016.01)

(52) U.S. Cl.
CPC .... *A61M 16/0463* (2013.01); *A61M 16/0816* (2013.01); *A61M 16/202* (2014.02); *A61B 2017/345* (2013.01); *A61B 2018/00166* (2013.01); *A61B 2018/00172* (2013.01); *A61B 2018/00273* (2013.01); *A61B 2018/00541* (2013.01); *A61B 2018/00577* (2013.01); *A61B 2018/00642* (2013.01); *A61B 2018/00708* (2013.01); *A61B 2018/00863* (2013.01); *A61B 2018/00898* (2013.01); *A61B 2018/00982* (2013.01); *A61B 2018/0212* (2013.01); *A61B 2018/0268* (2013.01); *A61B 2090/0808* (2016.02); *A61M 16/0833* (2014.02); *A61M 2205/14* (2013.01); *A61M 2205/276* (2013.01)

(58) Field of Classification Search
CPC ........... A61B 2018/00898; A61B 2018/00982; A61B 2018/0212; A61B 2018/0268; A61B 2090/0808; A61M 16/0463; A61M 16/0816; A61M 16/0833; A61M 16/202; A61M 2205/14; A61M 2205/276; A61M 16/0486; A61M 2016/0027–0042
See application file for complete search history.

(56) References Cited

U.S. PATENT DOCUMENTS

| | | | |
|---|---|---|---|
| 2003/0018326 A1* | 1/2003 | Abboud | A61B 18/02 606/20 |
| 2004/0078033 A1* | 4/2004 | Levin | A61B 18/02 606/20 |
| 2009/0192504 A1* | 7/2009 | Askew | A61B 18/0218 606/21 |
| 2009/0192505 A1 | 7/2009 | Askew et al. | |
| 2013/0253491 A1 | 9/2013 | Burr et al. | |
| 2015/0066005 A1 | 3/2015 | Fan et al. | |
| 2015/0306329 A1* | 10/2015 | Brown | A61M 16/0463 128/200.26 |
| 2016/0074628 A1* | 3/2016 | Smith | A61B 50/20 604/174 |
| 2019/0167197 A1* | 6/2019 | Abunassar | A61B 5/6852 |

\* cited by examiner

SYSTEMS AND METHODS TO ENSURE GAS EGRESS DURING CRYOTHERAPY

PRIORITY

This application claims the benefit of priority under 35 U.S.C. § 119 to U.S. Provisional Patent Application Ser. No. 62/468,631, filed Mar. 8, 2017, which is incorporated by reference herein in its entirety and for all purposes.

FIELD

The present disclosure relates generally to the field of cryotherapy. In particular, the present disclosure relates to cryotherapy systems that ensure egress of gas generated as a result of cryogen liquid delivered within a patient's body during cryotherapy procedures and, more particularly, the present disclosure relates to sensors for use with cryotherapy systems that include delivery catheters, wherein the systems ensure that egress of cryogen-induced gas from the patient's body is possible whenever the catheter is operating.

BACKGROUND

Cryoablation, as an example of cryotherapy, is a surgical procedure in which diseased, damaged or otherwise undesirable tissue (collectively referred to herein as "target tissue" and/or "treatment region") may be destroyed by local delivery of a cryogen spray. These systems along with other cryotherapy systems are typically referred to as cryoablation systems, cryospray systems, cryospray ablation systems, cryosurgery systems, cryosurgery spray systems and/or cryogen spray ablation systems. As typically used, "cryogen" refers to any fluid (e.g., gas, liquefied gas or other fluid known to one of ordinary skill in the art) with a sufficiently low boiling point (i.e., below approximately −153° C.) for therapeutically effective use during a cryogenic surgical procedure. Suitable cryogens may include, for example, liquid argon, liquid nitrogen and liquid helium. Pseudo-cryogens such as liquid carbon dioxide and liquid nitrous oxide that have a boiling temperature above −153° C. but still very low (e.g., −89° C. for liquid $N_2O$) may also be used.

For example, during operation of a cryospray ablation system, a medical professional (e.g., clinician, technician, physician, surgeon, etc.) directs a cryogen spray onto the surface of a treatment area via a cryogen delivery catheter. The medical professional may target the cryogen spray visually through a video-assisted device or endoscope, such as a bronchoscope, gastroscope, colonoscope, or ureteroscope. Cryogen spray exits the cryogen delivery catheter at a temperature ranging from 0° C. to −196° C. for $LN_2$, causing the target tissue to freeze or "cryofrost." As liquid cryogen exits the cryogen delivery catheter and impacts upon the target, it converts to a gaseous state with a significant increase in volume. For example, 1 cubic centimeter ($cm^3$) of liquid nitrogen converts to 694 $cm^3$ of nitrogen gas at body temperature. If not properly isolated and/or vented from the patient and allowed to progress further into the body from the treatment site, these expanding gases may cause undue distention and may have life-threatening consequences, including, for example, pneumothorax of the lungs and perforations of the upper or lower gastrointestinal (GI) tract.

In a cryoablation procedure in the trachea involving ventilation, an endotracheal (ET) tube with an ET tube adaptor on the proximal end of the tube may be placed in the trachea to facilitate breathing. In such conventional ventilation systems, the ventilator tube must be detached from the endotracheal tube adaptor in order for any internal gas within the patient to egress to the open atmosphere. Accordingly, various advantages may be realized by cryotherapy systems and methods as disclosed herein, which ensure an adequate pathway for venting of cryogen gas outside of the patient whenever the cryogen delivery catheter is operable.

SUMMARY

Embodiments of the present disclosure may include a sensor for use with a catheter that delivers cryogen gas within a body of a patient. The sensor may include a gas inlet at a patient side of the sensor that receives cryogen gas vented from the patient's body. The sensor may include a gas outlet at an atmosphere side of the sensor that vents cryogen gas out of the sensor to the atmosphere. The sensor may include a connection between the sensor and a console for the catheter, whereby the sensor is configured to ensure that egress of cryogen gas from the gas outlet is possible whenever the catheter is operable.

A sensor may include a valve that communicates with the atmosphere at the gas outlet when the valve is open. A connection may comprise a cable connected to the valve and the console. The cable may be controlled at the console by an actuator to open the valve automatically to the atmosphere when the catheter is operable. The cable may be a push-pull cable, and the actuator may be a linear actuator.

A sensor may include a flexure point that deflects upon attachment of a ventilator tube to the gas outlet. The connection may comprise a switch that is actuated upon deflection of the flexure point to convey a signal along the connection to the console preventing the catheter from operating.

A sensor may include a gas outlet that is configured to engage with a ventilator tube. The sensor may include a connection comprising an air pressure port having a first end for connection to a source of air, and a pressure relief opening on the gas outlet at a second end of the port. The pressure relief opening may be at least partially covered by the ventilator tube when the ventilator tube is engaged with the gas outlet, creating a threshold air pressure in the port that is measurable at the console to prevent the catheter from operating.

A sensor may include a manual vent valve that communicates with the atmosphere at the gas outlet. A valve position may correspond to the valve being open or closed, and may be communicated via a connection to a console to allow a catheter to respectively operate or not operate.

A sensor may include a gas inlet that is configured to mount to a ventilator tube inlet of an endotracheal tube adapter. A gas outlet may include a venting aperture that may not engage a ventilator tube. The sensor may include a switch that detects when the gas inlet is mounted to the endotracheal tube adapter. A connection when the switch is actuated may signal the console to allow operation of the catheter.

A sensor may include a ventilation end for engaging a ventilator tube. The sensor may include a compression switch disposed on a circumference of the ventilation end that is communicatively connected to a console for a catheter. The sensor may be configured to ensure egress of cryogen gas from the ventilation end whenever the catheter is operable. The switch may compress when the ventilation end is engaged with the ventilation tube communicating with the console to prevent the catheter from operating.

A sensor may include a compression switch on an outer circumference of a ventilation end. The sensor may include an endotracheal end for engaging an endotracheal tube adaptor. The sensor may include a compression switch on a circumference of the endotracheal end. The switch may be communicatively connected to a console. When the sensor is connected to the endotracheal tube adapter at the endotracheal end, the compression switch on the circumference of the ventilation end may actuate and may communicate to the console to allow the catheter to operate. The sensor may include a compression switch on an inner circumference of the endotracheal end.

A cryotherapy system may include a sensor, a console communicatively connected to the sensor, and a cryospray catheter communicatively connected to the console. The catheter may be configured to deliver cryogen gas within a body of a patient. The system may be configured to ensure that egress of cryogen gas from the sensor is possible whenever the catheter is operable. A system may include a sensor with a gas inlet at a patient side of the sensor that receives cryogen gas vented from the patient's body. The system may include a gas outlet at an atmosphere side of the sensor that vents cryogen gas from the sensor to the atmosphere.

A system may include a flexure point that deflects upon attachment of a ventilator tube to a gas outlet. A connection may include a switch that is actuated upon deflection of the flexure point to convey a signal along the connection to a console preventing a catheter from operating. A system may include a gas outlet that is configured to engage with a ventilator tube. A connection may comprise an air pressure port having a first end for connection to a source of air, and a pressure relief opening on the gas outlet at a second end of the port. The pressure relief opening may be at least partially covered by the ventilator tube when the ventilator tube is engaged with the gas outlet, creating a threshold air pressure in the port that is measurable at the console to prevent the catheter from operating.

A system may include a manual vent valve at the gas outlet that communicates with the atmosphere at the gas outlet, wherein a valve position corresponding to the valve being open or closed may be communicated via a connection to a console to allow a catheter to respectively operate or not operate. The gas inlet of a sensor may be configured to mount to a ventilator tube inlet of an endotracheal tube adapter. The gas outlet may include a venting aperture that is configured to not engage a ventilator tube. The sensor may include a compression switch that detects through compression of the compression switch when the gas inlet is mounted to the endotracheal tube adapter. The connection when the switch is compressed may signal the console to allow operation of the cryospray catheter.

A system may include a connection between a sensor and a console comprising a sensor wire that runs through an interface concentrically disposed onto a shaft of a catheter. The system may include a sensor wire retention clip concentrically disposed onto the shaft of the catheter to which the sensor wire may be removably clipped. The system may include a sensor that comprises a valve in fluid communication with the atmosphere. The console may include a linear actuator that may be communicatively connected to the valve via a push-pull cable. The linear actuator may actuate the push-pull cable to open the valve when the catheter is operable.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described. The description and terminology used herein is not intended to be limiting beyond the scope of the appended claims. Unless otherwise defined, all technical terms used herein have the same meaning as commonly understood by one of ordinary skill in the art to which the disclosure pertains.

Although embodiments of the present disclosure are described with specific reference to cryotherapy systems for use within the respiratory system, the sensor component may be useful in connection with other situations, or in connection with a variety of other body passageways, organs and/or cavities, such as the gastrointestinal system, vascular system, urogenital system, lymphatic system, neurological system and the like, where egress of gas or some other fluid from the body is restricted to a certain path and it is desired to insert a sensor in the path to ensure that egress is available whenever fluid is being delivered to the body or, alternatively, to confirm that fluid is not delivered to the body whenever egress is not available.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

As used herein, the term "passive venting" refers to unassisted egress of gases from within a body lumen to an external location, through a body lumen and natural orifice and/or through a tube or other device passing through the same, e.g., an ET tube, when a ventilator tube is not attached, as described above. As used herein, the term "active venting" refers to mechanically-assisted egress (e.g., via a suction source) of gases from with a body lumen to an external location through a catheter, endoscope, ventilator tube or other device.

The present disclosure generally provides cryotherapy systems configured to adequately and reliably vent cryogen gases, such as gases produced from cryospray systems from within a body lumen of a patient, such as from within the respiratory system of a patient. Exemplary cryotherapy systems in which the present disclosure may be implemented include, but are not limited to, those systems described commonly owned U.S. Pat. Nos. 9,820,797, 9,301,796, and 9,144,449 and U.S. patent application Ser. Nos. 11/956,890, 12/022,013, and 14/012,320, each of which are herein incorporated by reference in their entirety.

For example, with reference to a cryotherapy system utilizing a catheter that delivers cryogen gas with cryospray to the respiratory system, involving ventilation, an endotracheal tube may be placed in the trachea to facilitate breathing. A cuff at the distal end of the ET tube may be inflated into contact with opposing walls of the trachea in order to maintain the tube in place. An endotracheal tube adaptor may be placed on the proximal end of the tube. The adaptor has a ventilator tube inlet, and an access inlet through which an endoscope may be placed and inserted down through the ET tube to a target location. The ventilator tube may provide air or other gaseous mixture to the patient and measure the patient's breathing (this pathway from the ventilator tube inlet through the ventilator tube is referred to herein as the "ventilator airflow circuit"). The ET tube adapter also has an access inlet through which an endoscope is placed, such as a bronchoscope, to allow a medical professional to view the target tissue site to be treated. The access inlet may have a cover or seal that the endoscope can pass through, effectively occluding that inlet. Without use of a cover or seal, the scope may not completely occlude the access inlet. The endoscope is inserted through the access inlet and a cryogen delivery catheter may be inserted through the working channel of the endoscope. The catheter exits the endoscope and endotracheal tube distal to the cuff. During a cryospray application when the ventilator is connected, the gas is prevented by the inflated cuff from freely venting from the trachea and instead the gas must be actively vented back through the endoscope or passively vented up the ET tube outside of the endoscope. In the latter case, when the gas reaches the proximal end of the ET tube, if the ventilation tube is connected to the adaptor and the endoscope is within the access inlet, there may be little or no egress path for the gas to the atmosphere. Thus, there is no patient airway exposure to the atmosphere for gas egress. If ventilation is active as well, there may be positive pressure of oxygenated air traveling down the ET tube that may also inhibit or prevent passive venting of cryogen gas up the ET tube. In such conventional ventilation systems, during a cryoablation procedure, since cryospray gas egress is essential for cryotherapy system function and patient safety, a medical professional must remember to physically remove the ventilator tube before initiating cryoablation treatments. When the ventilator tube is removed, the cuff around the ET tube is generally controlled to deflate, which provides an additional path of egress for gas between the wall of the body lumen and the ET tube. Failure to remove the ventilator tube before or during operation of the catheter could cause undue gas to build up inside the patient and instruments, leading to system failure from cold gas build-up within the medical instruments and patient bodily injury such as distention. With the cuff deflated and the ventilator disconnected, egress is allowed between the ET tube and patient anatomy. Gas may egress in the space between the scope and the ET Tube inner diameter and around the outer diameter of the ET tube. Gas egress back through the catheter is generally not possible as it is actively spraying.

In various embodiments of the present disclosure, an operative console communicatively connected to a sensor of a cryotherapy system may ensure an adequate gas egress pathway by preventing cryoablation when the sensor signals and/or the console detects that there is an inadequate path for gas egress. For example, the sensor may prevent a medical professional from delivering cryogen through the delivery catheter when the ventilator tube is still connected or when a gas egress valve has not been opened. In this way, the sensor will not allow a medical professional to proceed with cryoablation without a means for the cryospray gas to adequately egress from the patient.

Embodiments of the present disclosure may include a sensor for use with a cryotherapy system, which may include a gas egress pathway with a gas inlet at an internal side of the sensor and a gas outlet at an atmosphere side of the sensor. Gas egress may occur from within the sensor first through the gas inlet and then through the gas outlet to the atmosphere outside the sensor. A connection between the sensor and a console that controls the cryospray catheter may ensure that a gas egress pathway is possible when the cryospray catheter is operable. If the sensor communicates to the console via the connection between the sensor and the console that there is not an open pathway for gas egress, the console may be configured to prevent the catheter from operating.

Figure 1:
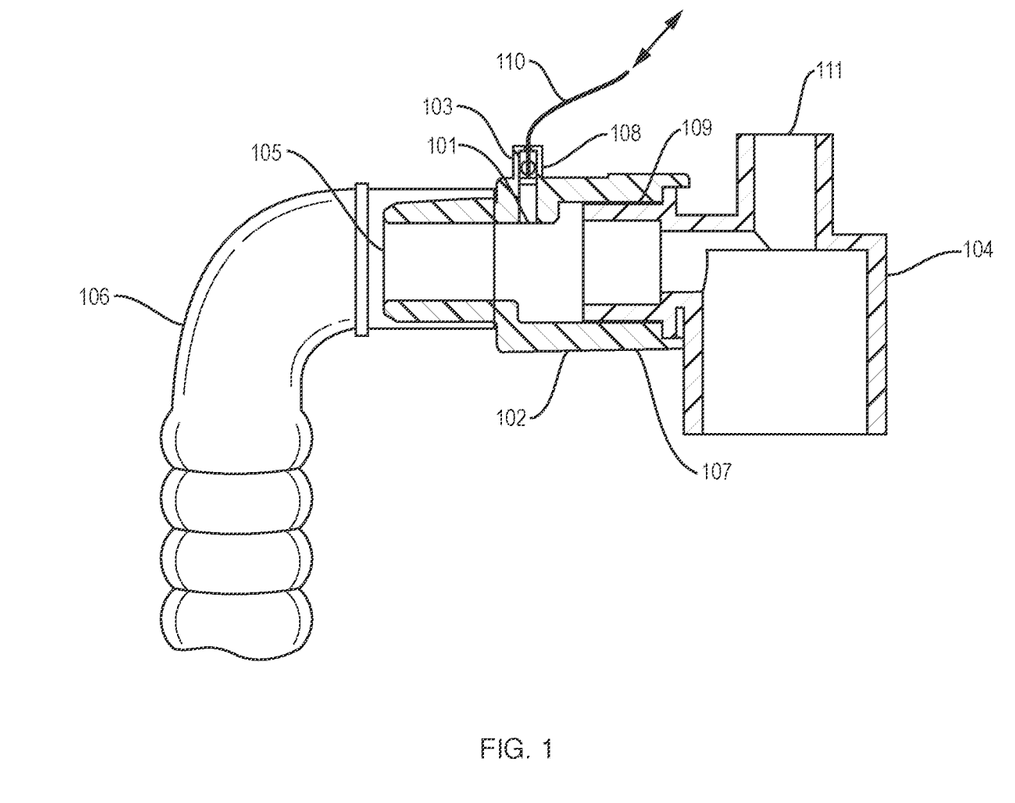
FIG. 1 illustrates a sensor device in accordance with an embodiment of the present disclosure including a valve.

Referring to FIG. 1, an example embodiment of the disclosure may include a sensor 102 with a gas inlet 101 at a patient side of the sensor 102, a gas outlet 103 at an atmosphere side of the sensor 102, a ventilator tube mount 105, and an adapter mount 107. The sensor 102 mounts onto an endotracheal tube adapter 104 at a ventilator tube inlet 109. The adapter mount 107 may include stepped-shoulders to abut against the endotracheal tube adapter 104. A ventilator tube 106 attaches to the ventilator tube mount 105. The ventilator tube mount 105 may include a tapered profile and a shoulder backstop that the ventilator tube 106 may abut against in a mounted state.

When the ventilator tube 106 is connected to the ventilator tube mount 105, the sensor 102 is a part of the ventilator airflow circuit, between the ventilator tube inlet 109 of the endotracheal tube adapter 104 and the ventilator tube 106. The sensor 102 includes a connection 110 between the sensor 102 and a console for control of a cryogen catheter that is mounted to the console and inserted into a patient's body through the endotracheal tube via an endoscope inserted into the access inlet 111 of endotracheal tube adaptor.

The sensor includes a valve 108 in fluid communication with the atmosphere. Various types of valves are suitable, as known in the art, including mechanically actuated valves.

The connection depicted is a cable 110 that is connected to the valve 108 at one end and to a console at the other end. The cable 110 may be a push-pull cable. The open and closed position of the valve 108 may be controlled by the cable 110 via an actuator on the console. Alternatively, there is a wireless connection between the console and the valve actuator, such that valve actuation may be controlled wirelessly. The actuator may be a linear actuator. The console may control the cable 110 to open the valve 108 automatically to the atmosphere when the catheter is operable. Gas egression may occur through a pathway from the internal gas inlet 101 side of the valve 108 to the external gas outlet 103 of the valve when the valve is open.

The console may be programmed to open the valve 108 automatically when necessary during cryotherapy treatments without user intervention by a software command that instructs an actuator to activate the cable 110, which in turn moves the valve 108 to the open position. When cryotherapy is interrupted or completed, a software command to move the valve 108 to the closed position may be issued. In this way, there is no need to detach the ventilator tube 106 at any point during the cryotherapy procedure since the valve 108 will allow the cryospray to egress when opened to the atmosphere.

Figure 2:
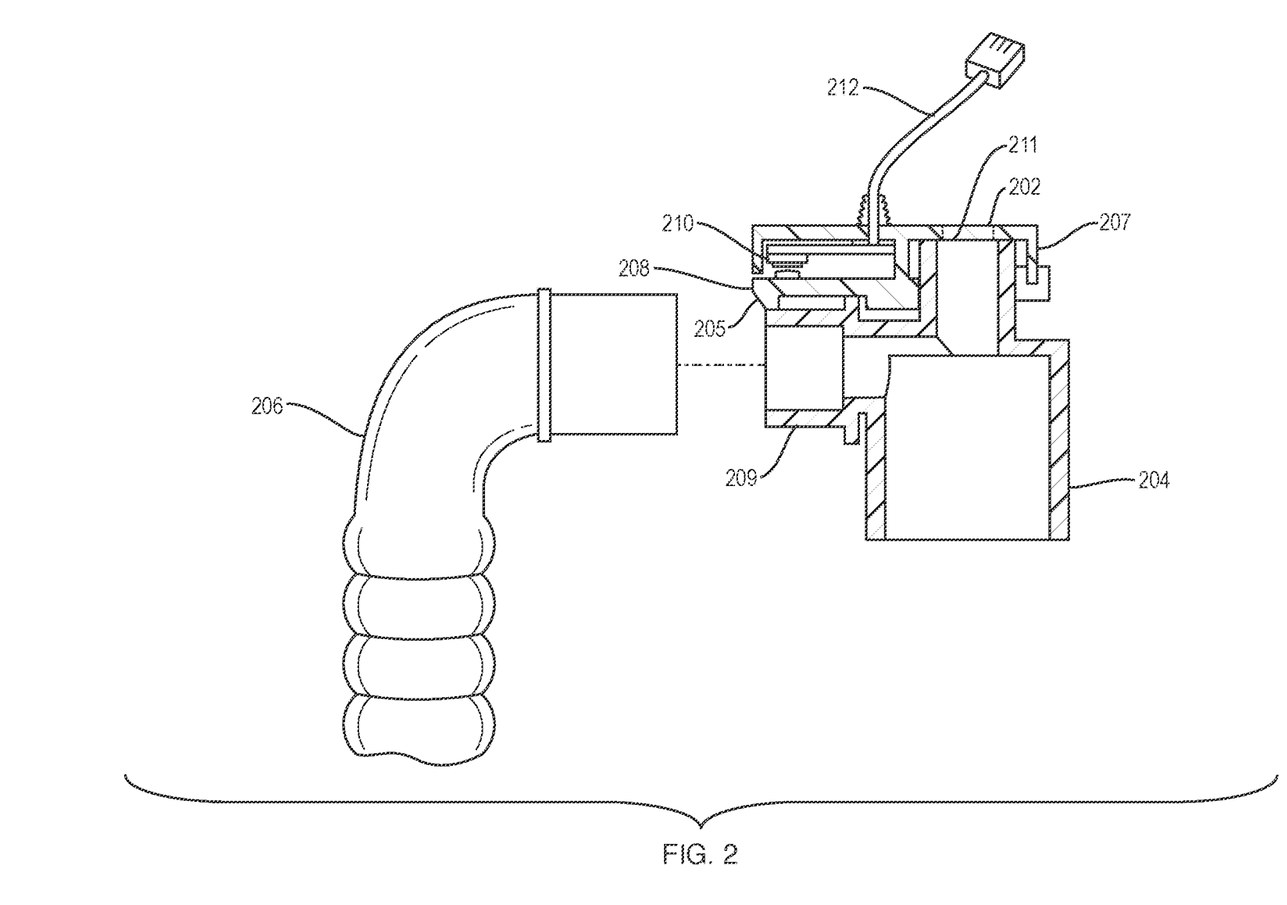
FIG. 2 illustrates a sensor device in accordance with an embodiment of the present disclosure including a switch.

Referring to FIG. 2, an example embodiment of the disclosure may include a sensor 202 with a ventilator tube mount 205 and an adapter mount 207. For gas egression, the gas inlet in this embodiment is the internal cavity of the endotracheal tube adapter 204 and the gas outlet is the ventilator tube inlet 209 of the endotracheal tube adapter. The sensor 202 is mounted to the endotracheal tube adapter 204 outside of the ventilator airflow circuit. The sensor 202 may be permanently attached to ensure use, but could be placed by a medical professional for each cryotherapy session. A circular aperture on the top surface of 202 allows a scope to pass through. The sensor 202 may include a flexure point 208 that a ventilator tube 206 engages by deflecting the flexure point upon attachment of the ventilator tube to the ventilator tube inlet 209 of the endotracheal adapter 204. Deflecting the flexure point 208 may close a switch 210 (such as an open limit switch) of the sensor 202. The switch 210 may communicate through a wire 212 to the console to prevent cryotherapy operation when the flexure point 208 is deflected, indicating that the ventilator tube 206 is attached to the ventilator inlet 209 of the endotracheal adapter 204. The flexure point 208 may accommodate a range of ventilator tube 206 outer diameters. The flexure point 208 may be an elongated arm with a slanted end to accept the ventilator tube 206. When the ventilator tube is not attached to the adaptor the flexure point is not deflected and the switch moves to an open position signaling to the console that the "gas outlet" of the sensor (the ventilator inlet of the adaptor) is open to egress of gas, and cryogen delivery may be operated. The ventilator tube mount 205 may snap onto or into an edge of the ventilator tube 206 as a safety feature.

Figure 3:
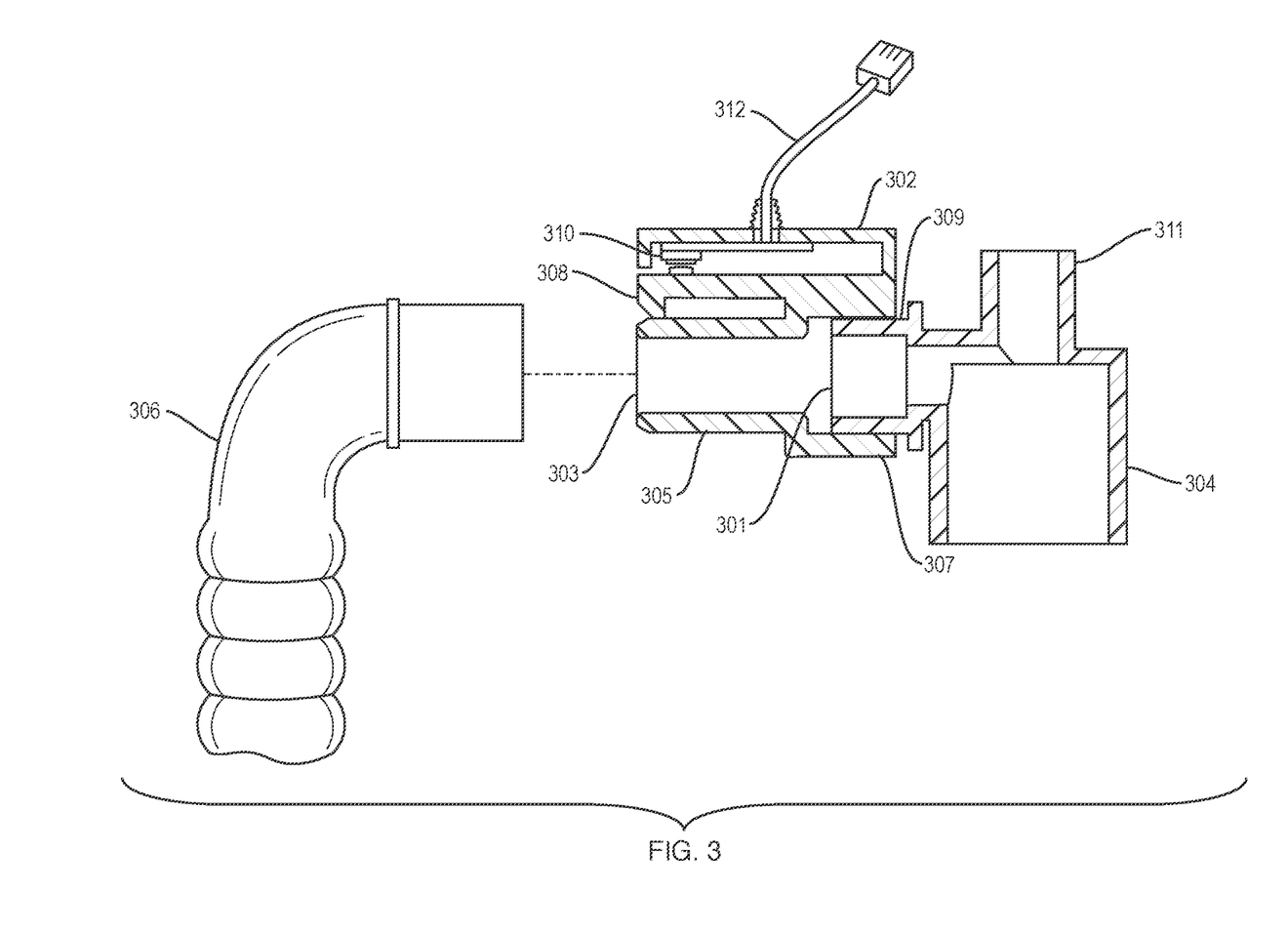
FIG. 3 illustrates a sensor device in accordance with a further embodiment of the present disclosure including a switch.

Referring to FIG. 3, an example embodiment of the disclosure may include a sensor 302 with a gas inlet 301 at a patient side of the sensor 302, a gas outlet 303 at an atmosphere side of the sensor 302, a ventilator tube mount 305, and an adapter mount 307. The sensor 302 mounts onto an endotracheal tube adapter 304 at a ventilator tube inlet 309. The adapter mount 307 may include stepped-shoulders to abut against the endotracheal adapter 304. A ventilator tube 306 attaches to the ventilator tube mount 305. The ventilator tube mount 305 may include a tapered profile and a shoulder backstop that the ventilator tube 306 may abut against in its mounted state. In this way, the sensor 302 becomes part of the ventilator airflow circuit between the ventilator tube inlet 309 and the ventilator tube 306. The sensor 302 may include a flexure point 308 that the ventilator tube 306 engages by deflecting it upon attachment to the sensor 302. Deflecting the flexure point 308 may close switch 310 (such as an open limit switch) of the sensor 302. The switch 310 may communicate through a wire 312 to the console to prevent cryotherapy operation when the flexure point 308 is deflected, indicating that the ventilator tube 306 is attached to the ventilator tube mount 305, blocking the gas outlet 303. The flexure point 308 may accommodate a range of ventilator tube 306 outer diameters.

Figure 4:
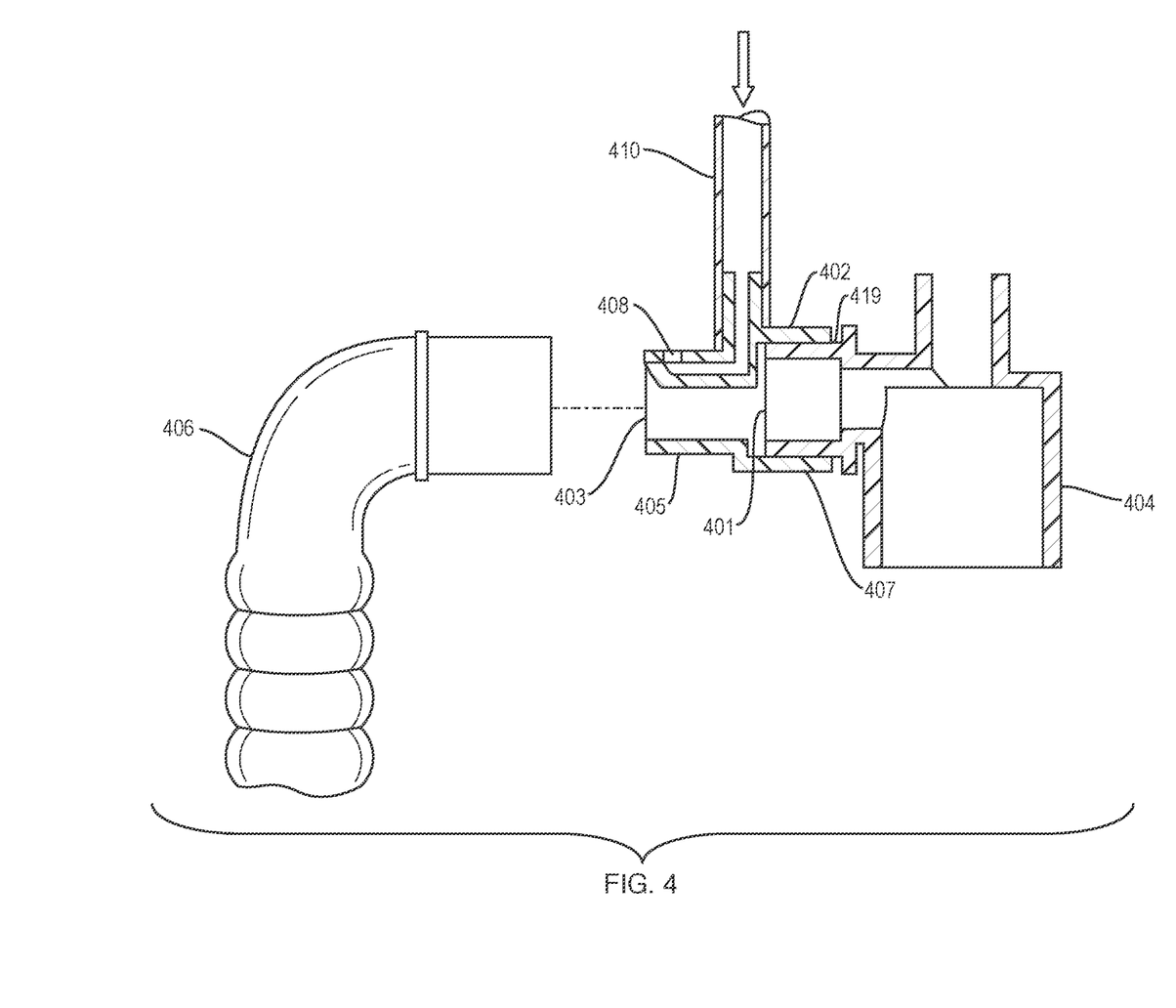
FIG. 4 illustrates a sensor device in accordance with another embodiment of the present disclosure including an air pressure port.

Referring to FIG. 4, an example embodiment of the disclosure may include a sensor 402 with a gas inlet 401 at a patient side of the sensor 402, a gas outlet 403 at an atmosphere side of the sensor 402, a ventilator tube mount 405, and an adapter mount 407. The sensor 402 mounts onto an endotracheal tube adapter 404 at a ventilator tube inlet 419. The adapter mount 407 may include stepped-shoulders to abut against the endotracheal adapter 404. A ventilator tube 406 attaches to the ventilator tube mount 405. In this way, the sensor 402 becomes part of the ventilator airflow circuit between the ventilator tube inlet 419 and the ventilator tube 406.

The sensor 402 may include a connection, which in FIG. 4 is an air pressure port 410 connected to the console at one end, with a pressure relief opening 408 on the sensor 402 that is at least partially covered by the ventilator tube 406 when the ventilator tube is attached to the ventilator tube mount. A console or some other source that communicates with the console supplies air through the air pressure port 410. Air pressure measured in the air pressure port 410 by the console, for example, above a predetermined threshold pressure, indicates that the ventilator tube 406 is connected and the console prevents cryotherapy operation. When the ventilator tube is disconnected, air pressure measured in the air pressure port 410 by the console, for example, will be below the predetermined threshold pressure, indicating that the ventilator tube 406 is disconnected. The console recognizes that egress of cryogen gas from the gas outlet 403 is possible and allows the catheter to operate.

Figure 5:
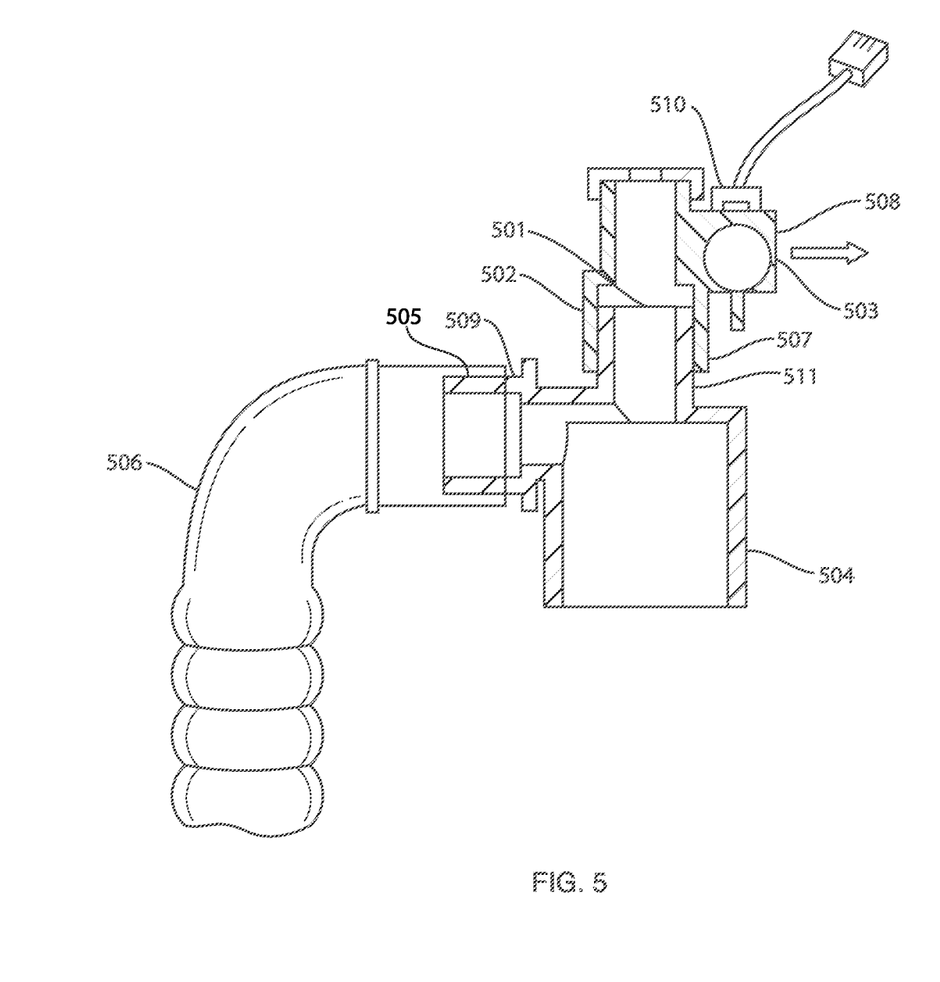
FIG. 5 illustrates a sensor device in accordance with an embodiment of the present disclosure including a valve.

Referring to FIG. 5, an example embodiment of the disclosure may include a sensor 502 with a gas inlet 501 at a patient side of the sensor 502, a gas outlet 503 at an atmosphere side of the sensor 502, an adapter mount 507, and an endoscope opening 505. The sensor 502 mounts onto an endotracheal tube adapter 504 at an access inlet 511. The sensor 502 may include a manual vent valve 508 that fluidly communicates with the atmosphere. When gas egress is demanded, a medical professional may open the valve 508, allowing cryospray gases to egress through the gas inlet side 501 of the valve 508, and egress through the gas outlet 503 side of the valve 508 to atmosphere. A removable gasket, which typically may be found on the top of the ET tube adapter that the scope passes through to create a seal, may be relocated to the endoscope opening 505 to provide a seal around the endoscope passing therethrough. Gas egress is possible between the endoscope and the access inlet 511. Closing the valve 508 may seal the egress pathway for uses such as, for example, to ventilate. The sensor may have a valve position sensor 510 that may detect when valve 508 is in an open position, allowing for a gas egression pathway (e.g. the gas outlet), or in a closed position. A connection to a console may communicate the position of the valve. In this embodiment, the ventilator tube 506 does not need to be removed from the ventilator air circuit and may remain on the ventilator tube mount 509. The console may not allow for cryospray operation when ventilation of oxygen through the ventilator air circuit was occurring, and open valve 508 to ventilate gas during cryospray procedure when oxygen ventilation is not occurring.

Figure 6:
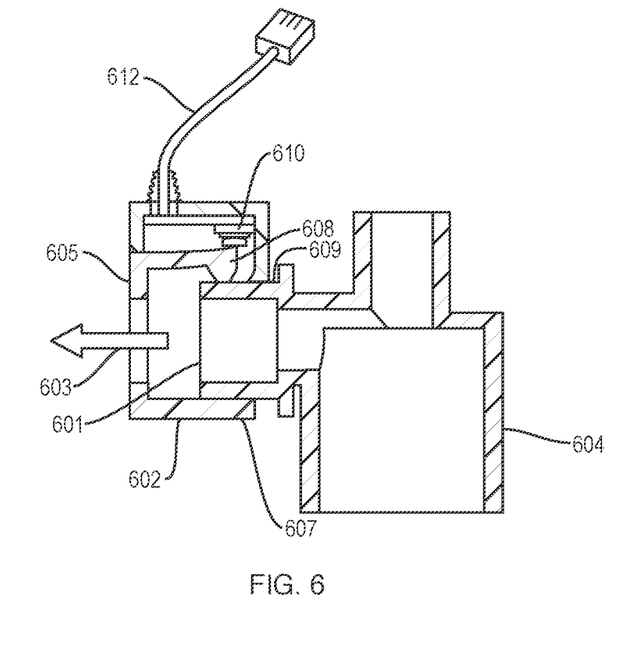
FIG. 6 illustrates a sensor device in accordance with an embodiment of the present disclosure including a switch.

Referring to FIG. 6, an example embodiment of the disclosure may include a sensor 602 with a gas inlet 601 at a patient side of the sensor 602, a gas outlet 603 at an atmosphere side of the sensor 602, a venting aperture 605 that is dimensioned such that it will not engage a ventilator tube (not shown), and an adapter mount 607. The sensor 602 mounts onto an endotracheal tube adapter 604 at a ventilator tube inlet 609. The gas outlet 603 is at the venting aperture 605 and is open to allow for the egress gases in the direction of the arrow. The venting aperture 605 may be sized and/or shaped to not allow a ventilator tube to mount to it. The opposing gas inlet 601 end of the sensor 602 may be mounted to the ventilator tube inlet 609 of the endotracheal tube adapter 604 after the ventilator tube has been removed.

In this way, the sensor 602 may only be installed once the ventilator tube has been removed, allowing for adequate gas egress through the venting aperture 605 of the sensor 602. The sensor 602 has a switch 610 that is triggered when the adapter mount 607 is concentrically mounted to the ventilator tube inlet 609 of the endotracheal tube adapter 604. The switch 610 may be triggered by a flexure point 608 on the sensor 602. This flexure point 608 may be an elongated arm with an angled end that may engage a variety of outer diameters of ventilator tube inlets for endotracheal tube adaptors. The switch 610 may communicate with a console via a wired connection 612. When a cryogen catheter is operable and gas egress is demanded, the medical professional may detach the ventilator tube and attach the sensor 602. When the sensor is attached, the flexure point presses against and closes switch 610, which in turn sends a signal to the console that egress is possible and the cryogen catheter will be allowed to operate. Conversely, cryotherapy operation will be prevented by the console unless the switch 610 on the sensor 602 indicates that the sensor has been installed, ensuring adequate gas egression.

Figure 7A:
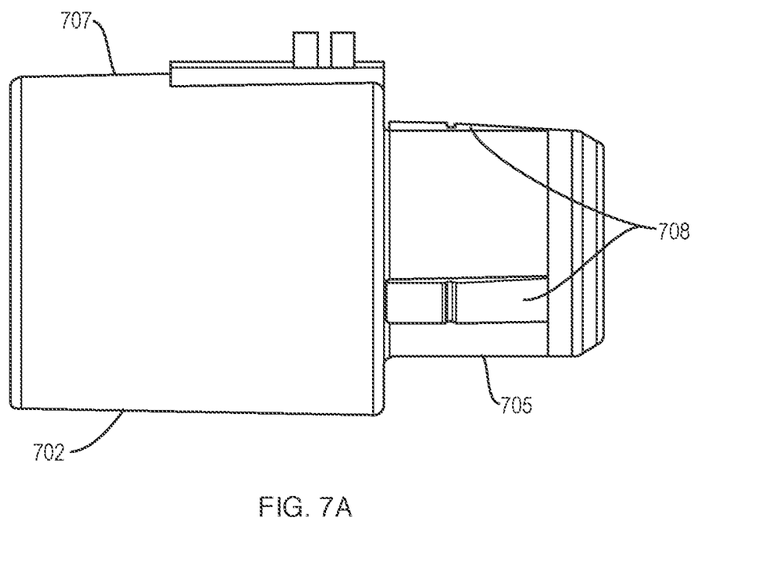
FIGS. 7A and 7B illustrate a sensor device in accordance with an embodiment of the present disclosure, including two switches.
Figure 7B:
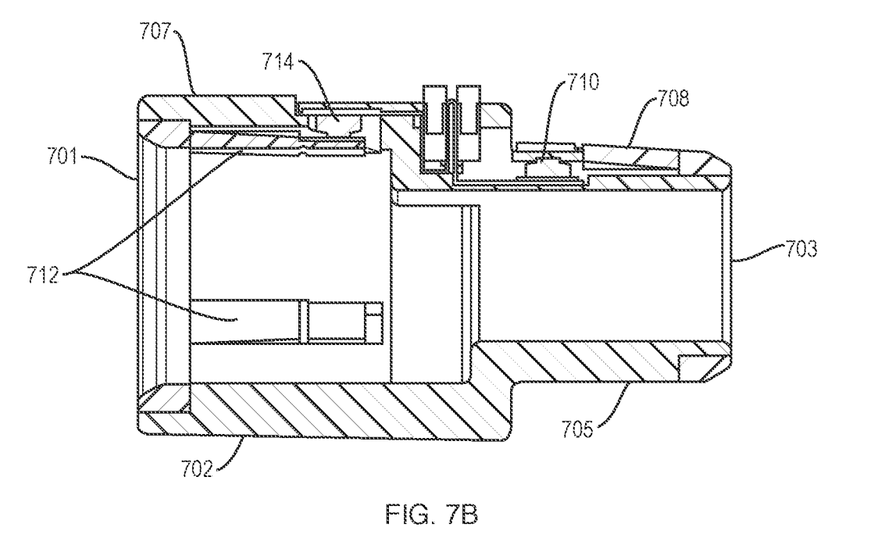

Referring to FIGS. 7A and 7B, an example embodiment of the disclosure may include a sensor 702 with a gas inlet 701 at a patient side of the sensor 702, a gas outlet 703 at an atmosphere side of the sensor 702, a ventilator tube mount 705, and an adapter mount 707. The sensor 702 mounts onto an endotracheal tube adapter (not shown) via the adapter mount 707. A ventilator tube (not shown) attaches to the ventilator tube mount 705. The ventilator tube mount 705 may include a tapered profile and a shoulder backstop that the ventilator tube may abut against in its mounted state. Once installed onto the endotracheal adapter, the sensor 702 may sense when it is connected to the adapter, as well as to the ventilator tube. The sensor 702 may include an outer radial compression 708 feature on a tapered outer circumference of ventilator tube mount 705 that covers a ventilator pressure switch 710, which may be a compression switch. A ventilator tube may circumferentially mount onto the ventilator tube mount 705 of the sensor 702, which engages an outer radial compression feature 708 when mounted. The outer radial compression feature 708 is able to compress the ventilator switch 710. There may be multiple outer radial compression features 708 in a circumferential pattern around the sensor. Connection points for the sensors may communicate with the console. When switch 710 is compressed, the sensor 702 may communicate with a console that a ventilator tube is attached to the sensor 702.

The opposing end of the sensor 702 may be adapter mount 707 having an inner radial compression feature 712 on a tapered inner circumference of the endotracheal end. An endotracheal tube adapter may circumferentially mount into the endotracheal end of the sensor 702 that engages the inner radial compression feature 712. The inner radial compression feature 712 may cover an endotracheal pressure switch 714, which may be a compression switch, that communicates with the console that an endotracheal tube adapter is attached when the switch 714 is compressed.

The sensor 702 prevents initiation of a cryoablation procedure unless the sensor 702 detects that it is attached to the endotracheal tube adapter and that the ventilator tube is not attached. When the endotracheal pressure switch is compressed (i.e., the endotracheal adapter is attached) and the ventilator switch is not compressed (i.e., the ventilator has been disconnected), an adequate gas egression pathway exists and the console may permit cryospray operation. If either of these conditions do not exist, then the console that the sensor is connected to may not permit cryospray operation. These outer and inner radial compression features 708 and 712 may be angled to aid in creating a tight fit for the ventilator tube and endotracheal adapter to ensure attachment to the sensor 702.

The various sensor embodiments may communicate with the console via a connection that may be a communicative wire. Wire management is important during medical procedures to reduce hazardous snags and entanglements. Typical procedures may use a bronchoscope attached to the endotracheal tube adapter and may contain the cryoablation medical instruments such as a cryospray catheter and/or endoscope. The catheter may extend from the bronchoscope to the console in order to supply gas and/or to communicate with the instruments.

Figure 8:
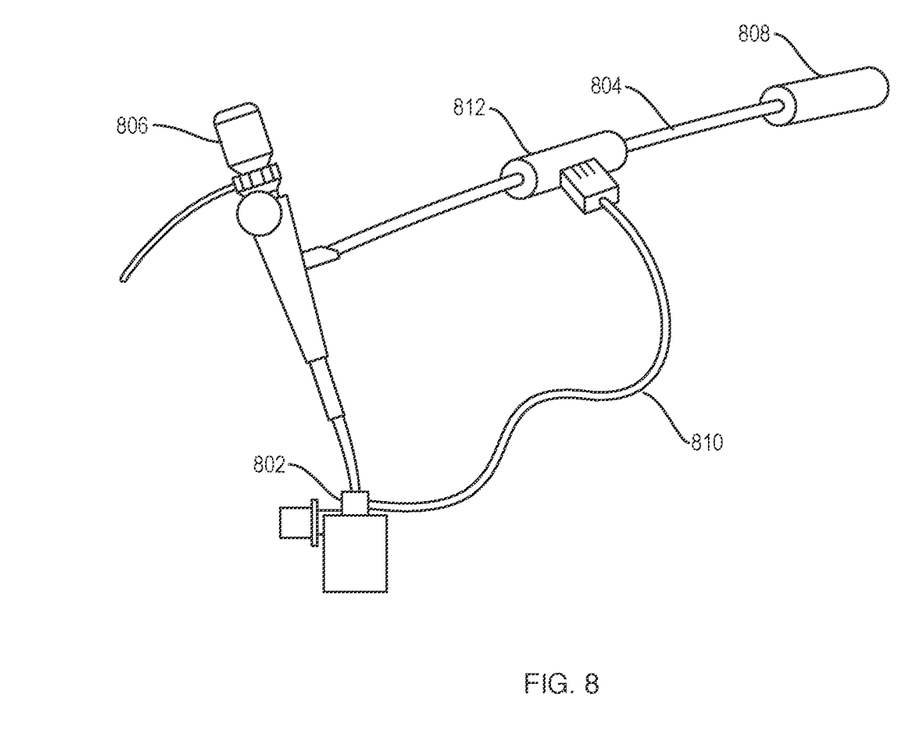
FIG. 8 illustrates a sensor device in accordance with an embodiment of the present disclosure including a sensor wire connector on a catheter.

Referring to FIG. 8, an example embodiment of the disclosure may include an interface 812 concentrically disposed onto the catheter 804 that extends out of the bronchoscope 806 and connects to the console via a console connector 808. A sensor wire 810 may connect the sensor 802 communicatively with the catheter 804 via the interface 812. In this way the wire 810 need not be longer than the distance from the sensor 802 to the interface 812. This wire pathway to interface 812 is shorter than the distance from the sensor 802 to the console. A shorter length of wire 810 decreases the chances of snags and entanglements.

Figure 9:
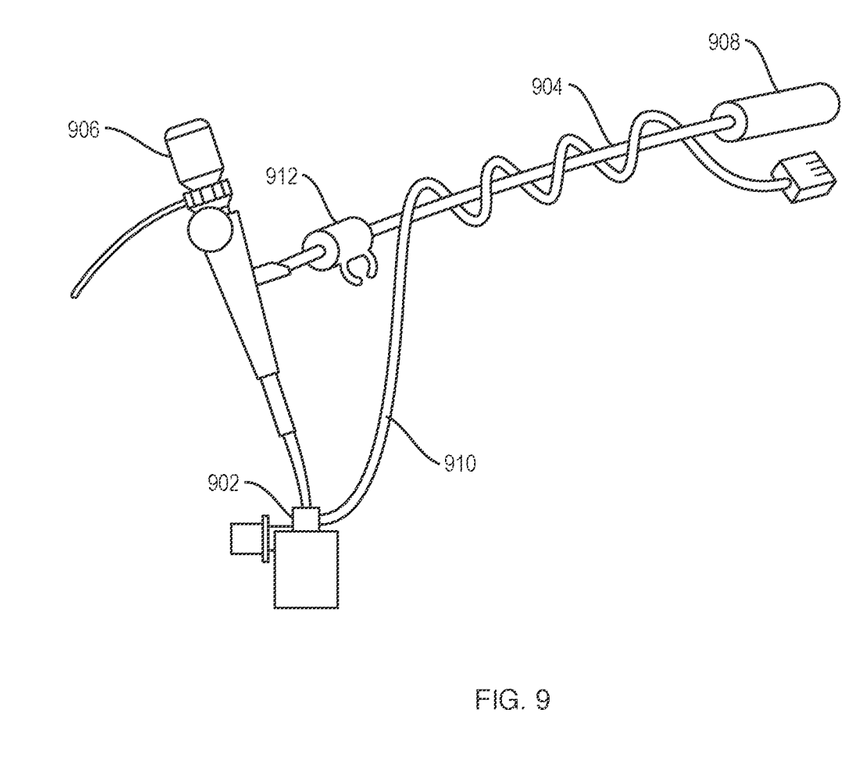
FIG. 9 illustrates a sensor device in accordance with an embodiment of the present disclosure including a sensor wire clip.
Figure 10:
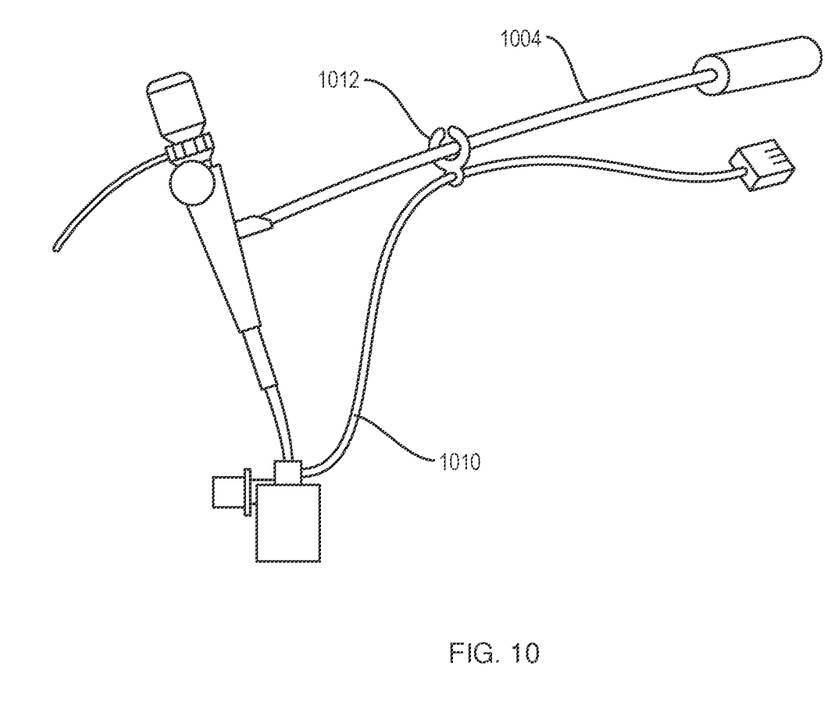
FIG. 10 illustrates a sensor device in accordance with another embodiment of the present disclosure including a sensor wire clip.

Referring to FIG. 9, an example embodiment of the disclosure may include a catheter 904 leading from a bronchoscope 906 to a console connector 908 that may mate with a gas egress sensor 902. The catheter may include a sensor wire retention clip 912 that the sensor 902 may removably clip to until the medical professional chooses to install the sensor 902 onto the endotracheal tube adapter. The sensor wire 910 may be coiled around the section of the catheter 904 between the bronchoscope 906 and the console connector 908. Additionally or alternatively, referring to FIG. 10, a sensor wire management clip 1012 may be attached to a section of the catheter 1004 to hold the wire 1010 and prevent it from hanging loose where it may snag on something or become entangled.

In one or more cryotherapy procedures using various of the sensors described above and otherwise, in accordance with the present disclosure, a medical professional may attach a sensor to either a ventilation tube inlet or access inlet of an endotracheal tube adapter. The medical professional may connect the sensor to a console, which, for example, may be a wired connection. If the connection is an air port, the medical professional may attach the port to an air source. Prior to operating the cryospray catheter, the medical professional may check that there is an adequate pathway for gas egression, for example, opening a valve. One or more compression switches may exist on the sensor that may automatically signal to the console whether they are engaged (e.g. compressed) or not. The console may permit and/or the medical professional may proceed with cryospray catheter operation. Once a cryotherapy session has completed, the gas egress may be shut and the patient may continue to receive ventilation (e.g. removing the sensor and replacing the ventilation tube).

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A sensor for use with a catheter that delivers cryogen gas out of the catheter within a body of a patient, comprising:
   a gas inlet at a patient side of the sensor that receives cryogen gas vented from the patient's body;
   a gas outlet at an atmosphere side of the sensor that vents cryogen gas out of the sensor to the atmosphere; and
   a connection between the sensor and a console for the catheter, whereby the sensor is configured to ensure that egress of cryogen gas from the gas outlet is possible whenever the catheter is operable.

2. The sensor of claim 1, wherein:
   the sensor includes a switch that detects when the gas inlet is mounted to the endotracheal tube adapter; and
   wherein the connection when the switch is actuated signals the console to allow operation of the catheter.

3. The sensor of claim 1, wherein the gas inlet is configured to reversibly mount to an endotracheal tube adapter.

4. The sensor of claim 1, further comprising a flexure point that deflects upon attachment of an endotracheal tube adapter.

5. The sensor of claim 4, wherein the flexure point comprises an elongated arm and an angled end configured to engage the endotracheal tube adaptor.

6. The sensor of claim 4, wherein the connection comprises a switch that is actuated upon deflection of the flexure point to convey a signal along the connection to the console permitting operation of the catheter.

7. The sensor of claim 6 wherein deflection of the flexure point closes the switch.

8. The sensor of claim 1, wherein the gas outlet comprises a venting aperture dimensioned such that it will not engage a ventilator tube.

9. The sensor of claim 1, wherein the connection between the sensor and the console comprises a sensor wire that runs through an interface concentrically disposed onto a shaft of the catheter.

10. A cryotherapy system, comprising:
    a sensor;
    a console communicatively connected to the sensor; and
    a cryospray catheter communicatively connected to the console, the catheter configured to deliver cryogen gas out of the catheter within a body of a patient, whereby the system is configured to ensure that egress of cryogen gas from the patient's body and through the sensor is possible whenever the catheter is operable.

11. The system of claim 10, wherein the sensor further comprises:
    a gas inlet at a patient side of the sensor that receives cryogen gas vented from the patient's body; and
    a gas outlet at an atmosphere side of the sensor that vents cryogen gas from the sensor to the atmosphere.

12. The system of claim 11,
    wherein: the gas inlet of the sensor is configured to mount to a ventilator tube inlet of an endotracheal tube adapter; the gas outlet includes a venting aperture that is configured to not engage a ventilator tube; and the sensor includes a compression switch that detects through compression of the compression switch when the gas inlet is mounted to the endotracheal tube adapter; and
    wherein the connection when the switch is compressed signals the console to allow operation of the cryospray catheter.

13. The system of claim 11, wherein the connection between the sensor and the console comprises a sensor wire that runs through an interface concentrically disposed onto a shaft of the catheter.

14. The system of claim 13, further comprising a sensor wire retention clip concentrically disposed onto the shaft of the catheter to which the sensor wire may be removably clipped.

15. The system of claim 10, wherein the sensor further comprises a flexure point that deflects upon attachment of an endotracheal tube adapter.

16. The system of claim 15, wherein the flexure point comprises an elongated arm and an angled end configured to engage the endotracheal tube adaptor.

17. The system of claim 15, wherein the connection comprises a switch that is actuated upon deflection of the flexure point to convey a signal along the connection to the console permitting operation of the catheter.

18. The system of claim 10, wherein the sensor further comprises a venting aperture dimensioned such that it will not engage a ventilator tube.

19. The system of claim 10, further comprising a connection between the sensor and the console, the connection comprising a sensor wire that runs through an interface concentrically disposed onto a shaft of the catheter.

* * * * *